United States Patent [19]
Finley

[11] Patent Number: 5,603,243
[45] Date of Patent: Feb. 18, 1997

[54] IMPROVEMENTS IN OR RELATING TO ALIGNMENT APPARATUS

[75] Inventor: Patrick A. Finley, Beaconsfield, United Kingdom

[73] Assignee: Armstrong Projects Limited, United Kingdom

[21] Appl. No.: 481,490

[22] PCT Filed: Nov. 11, 1994

[86] PCT No.: PCT/GB94/02477

§ 371 Date: Jul. 11, 1995

§ 102(e) Date: Jul. 11, 1995

[87] PCT Pub. No.: WO95/13018

PCT Pub. Date: May 18, 1995

[30] Foreign Application Priority Data

Nov. 11, 1993 [GB] United Kingdom ............... 9323259

[51] Int. Cl.[6] .................... B25J 9/10; G05G 11/00
[52] U.S. Cl. .................. 74/490.07; 74/490.03; 33/1 M; 248/124.1; 901/16; 901/23
[58] Field of Search .............. 74/490.01, 490.03, 74/490.07; 33/1 M; 248/124.1, 133, 371; 901/16, 23

[56] References Cited

U.S. PATENT DOCUMENTS 4,566,346  1/1986  Petiteau ........................ 901/16 X
5,107,839  4/1992  Houdek et al. ................. 128/653.1
5,165,296  11/1992  Yanagisawa ..................... 901/16 X

FOREIGN PATENT DOCUMENTS

0018166A1  10/1980  European Pat. Off. .
276143     6/1913   Germany .
4029590A1  7/1991   Germany .
WO91/16620 10/1991  WIPO .

OTHER PUBLICATIONS

"Bio-Engineering Approach to Sterotactic Surgery of the Brain," *Proceedings of the Institution of Mechanical Engineers*, B. H. Dawson et al, vol. 183, No. 15, 1968, pp. 281–292.

*Primary Examiner*—Allan D. Herrmann
*Attorney, Agent, or Firm*—Westman, Champlin, & Kelly, P.A.

[57] ABSTRACT

An alignment apparatus for aligning x-ray images with a predetermined set of axes comprises means defining the axes in the form of a support arrangement which supports, at predetermined positions in space, located in at least two predetermined planes, a plurality of elements which are opaque to ex-radiation. An apparatus is also described for aligning an end effector comprising two spaced guide frames each having two parallel guide members with a carriage for movement along each of the guide members, the carriages being inter-connected by cross members, further carriages being mounted on the cross members, the further carriages supporting the end effector for guide means.

4 Claims, 2 Drawing Sheets

IMPROVEMENTS IN OR RELATING TO ALIGNMENT APPARATUS

BACKGROUND OF THE INVENTION

THE PRESENT INVENTION relates to alignment apparatus. The invention will be described with reference to alignment apparatus used in the context of a medical apparatus and, in particular, to a robotically-controlled medical apparatus, but it is to be understood that the alignment apparatus of the invention may find different applications.

SUMMARY OF THE INVENTION

Two embodiments of alignment apparatus will be described, one comprising an apparatus intended to align an X-ray image with predetermined axes, and the other comprising an apparatus to align an end operator with a predetermined direction and a predetermined point in three dimensional space.

DESCRIPTION

According to one aspect of this invention there is provided an alignment apparatus for aligning X-ray images with a predetermined set of axes, comprises means defining the said set of axes, said means comprising a support arrangement adapted to support, at predetermined positions in space, located in at least two predetermined planes, a plurality of elements which are substantially opaque to extradiation.

Preferably the apparatus comprises two components, the components being located in orthogonal planes, each component supporting a plurality of said elements.

Conveniently each component is made of a material which is substantially transparent to ex-radiation.

Advantageously each component supports a plurality of said elements in a regular orthogonal array within the component.

Preferably the said elements are present, within each component, as a plurality of rows of evenly spaced elements.

Advantageously within each component there are four rows of elements which, when viewed axially, are located at the corners of a square or rectangle, there being at least three elements in each row.

Conveniently the said elements are of different size, different density relative to absorption of extradiation and/or of different shape to enable the images of the members to be identified.

Advantageously the first of said planes is horizontal and the second of said planes is vertical, means being provided to take an X-ray photograph both vertically and horizontally through said elements.

According to another aspect of this invention there is provided an apparatus for aligning an end effector or guide for an end effector with a predetermined point in space at a predetermined orientation, said apparatus comprising a first guide frame and a second guide frame, the first guide frame comprising two substantially vertically extending guide members, a respective carriage present for sliding movement along each of the guide members and a substantially horizontal cross-member inter-connecting the carriages, there being a further carriage mounted for horizontal movement on said second horizontal cross-member and a second frame of similar design spaced from the first frame but being in a plane parallel thereto, the second frame comprising two substantially vertical members each provided with a respective carriage for vertical sliding movement on the respective vertical member, the two carriages being inter-connected by a second horizontal cross-member having thereon a second carriage for horizontal sliding movement on said second horizontal cross-member, the two carriages mounted for horizontal movement supporting guide means or an end effector.

Preferably drive means are provided to drive the carriages to selected positions.

Conveniently the drive means for the carriages are computer controlled.

The computer may be provided with data from an alignment apparatus of the type broadly described above.

DESCRIPTION OF THE DRAWINGS

In order that the invention may be more readily understood, and so that further features thereof may be appreciated, the invention will now be described, by way of example, with reference to the accompanying drawings in which.

DETAILED DESCRIPTION OF THE PREFERRED EMBODIMENTS

Figure 1:
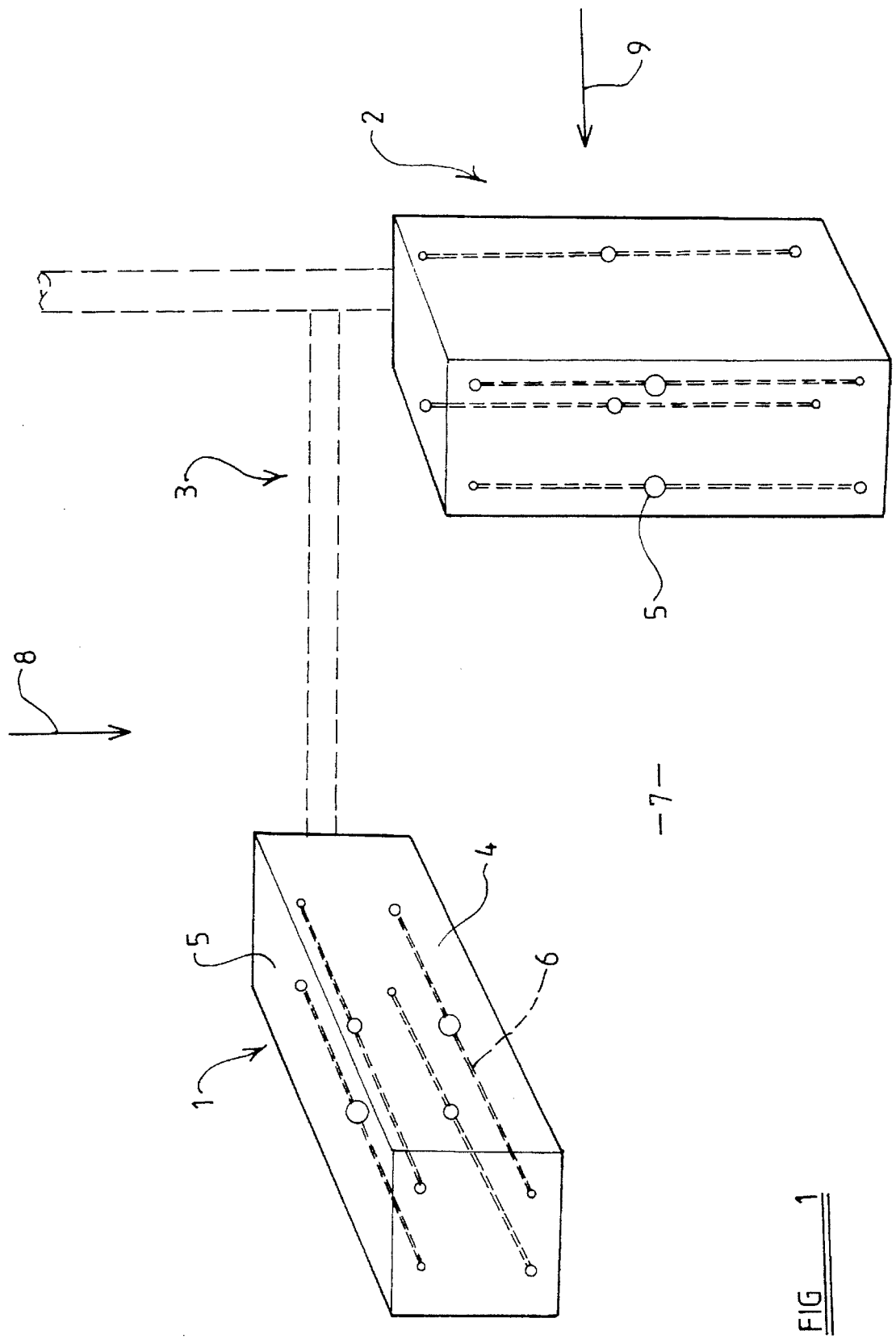
FIG. 1 is a diagrammatic prospective view of one embodiment of an alignment apparatus in accordance with the invention.

FIG. 1 illustrates an apparatus for use in aligning an item shown in an X-ray images with predetermined axes, or, in other words, for determining the precise position and orientation of an item shown in X-ray images relative to predetermined axes.

It is often very desirable to be able to determine the position of an X-ray image relative to predetermined axes. For example, if a medical patient is resting on an operating table and is to be operated on solely by or with the assistance of a medical robot, it is essential that the robot be provided with precise details as to the position of the relevant part of the patient, on the operating table, and the orientation of that part of the patient, those details being provided with reference to fixed predetermined axes. The robot may, for example, be required to align a drill, or a guide for a drill, precisely with a particular part of the patient, with the axes of the drill having a predetermined orientation.

Whilst, when a patient is resting on an operating table, it is possible to measure with accuracy the position of the exterior parts of the patient, but often the parts of the patient that are of most importance are interior parts, such as the bones of the patient.

Whilst it is possible to take X-ray images of a patient, unless very expensive C.A.T. (Computer Aided Tomography) apparatus is utilised, such X-ray images do not immediately provide an accurate indication as to the precise location of the various parts of the body shown in the X-ray images. There are various reasons for this, resulting from the fact that the X-ray source and the X-ray plate are not, generally speaking, located in a precisely predetermined position, and also arising from the fact that the beam from an X-ray source is generally a "fan" beam, with the beam diverging from the X-ray tube towards the image-receiving plate. Thus the image received by the plate is not necessarily a completely accurate image, but is enlarged and possibly distorted and/or displaced by the nature of the fan-beam.

Whilst it is possible to take X-ray images from two orthogonal directions it is often difficult to interpret those images to provide an accurate indication of the precise spatial position and orientation of the parts of the patient shown in the images.

FIG. 1 illustrates alignment apparatus which, when utilised as will now be described, reduces the difficulties experienced utilising the prior art techniques.

Referring to FIG. 1 the essential parts of an alignment apparatus are illustrated. The alignment apparatus comprises two alignment components 1, 2, which will be described in greater detail, which are held in position by an appropriate supporting framework 3. The supporting framework may be of any desired design and will thus not be described in detail since the sole function of the supporting framework 3 is to support the alignment components 1, 2 in the illustrated position, with the components 1, 2 preferably being located in a predetermined position relative to the upper surface of an operating table, and preferably also being located in a predetermined position relative to a medical robot which is to be utilised in performing an operation on a patient resting on the operating table.

The alignment components 1, 2 are each of elongate form and are located orthogonally, with the alignment component 1 having a substantially horizontal central axis and the alignment component 2 having a substantially vertical central axis.

Each alignment component comprises a rectangular block 4 of a material that is substantially transparent to X-rays. This material may comprise plastic material, but other materials may be utilised.

Mounted within each block 4 are a plurality of elements such as balls 5 made of a material that is opaque to X-rays. The balls may be made of metal or some other material that absorbs X-rays. Preferably the balls 5 are of different sizes relative to each other or are designed to absorb different quantities of X-rays, or are fabricated to be of different shapes, so that the images of the balls 5 may be recognised individually on an X-ray plate.

In each block 4 there are twelve balls 5. The balls are arranged in four axially extending rows 6. The ends of the rows 6, when viewed axially, form a square array. Each row is provided with three balls, the balls being uniformly spaced.

Referring to FIG. 1 it can be seen that the alignment components 1 and 2 are located adjacent an area of space 7 which, in use of the illustrated arrangement, in the manner presently being described by way of example, will contain part of a patient. A first X-ray image is taken of that part of the patient by directing an X-ray beam downwards in the direction indicated by the arrow 8, and a second X-ray image is taken by directing an X-ray beam horizontally in the direction indicated by the arrow 9.

In each of the resultant X-ray plates there will be images of the balls 5 present in both of the alignment components 1 and 2. Since the orientation and spacing of these elements is known, it is possible for appropriate calculating means, such as a computer, to calculate details of the divergence of the fan beam and consequently for the calculating means to determine the precise position and precise orientation of the parts of the patient present within the X-ray image, with reference to the axes defined by the alignment components 1 and 2.

It is envisaged, therefore, that the two X-ray images would be exhibited on an appropriate computer screen, and using a mouse or other equivalent means, a line of action would be marked on the screen. For example, if the screen showed a bone and it was necessary to drill a channel or opening into the bone, an appropriate line could be marked on each of the X-ray images present on the screen to show the precise position and direction of the line of action relative to the bone. Using the images of the various balls present in the alignment computers 1 and 2, a computer could then calculate, with reference to the axes effectively defined by the alignment components, the precise position and orientation to be occupied by the drill at the commencement of the drilling operation.

Whilst this embodiment has been described with specific reference to aligning images of part of a patient with predetermined axes, the described apparatus could be used for other purposes.

Figure 2:
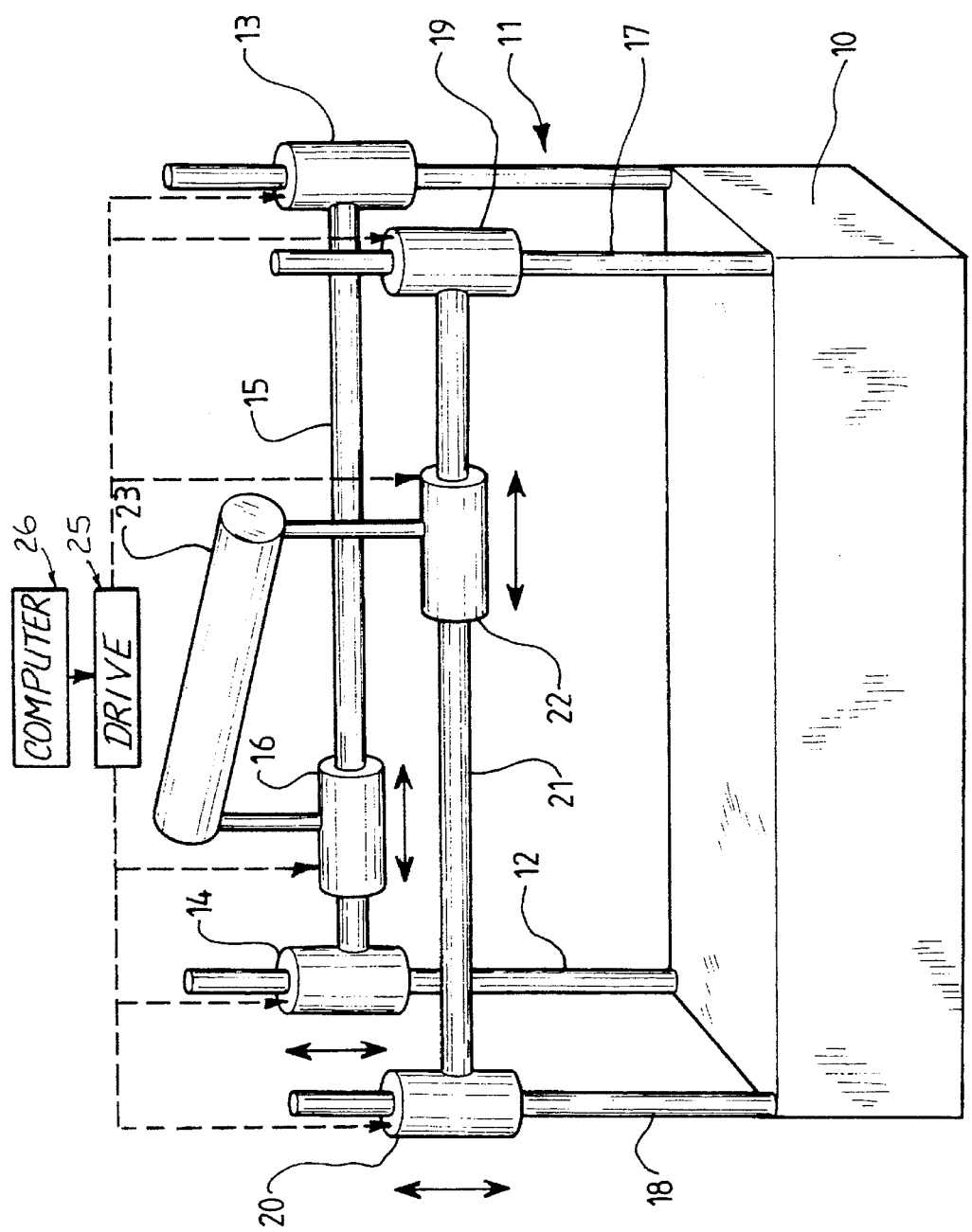
FIG. 2 is a diagrammatic perspective view of an alternative form of alignment apparatus in accordance with the present invention.

Reference will now be made to FIG. 2 of the accompanying drawings which illustrates an alignment apparatus in the form of an apparatus adapted to align a guide in a predetermined manner.

Whilst apparatus of the type shown in FIG. 2 may have many applications, the apparatus shown in FIG. 2 may be specifically intended for use in guiding a drill to be actuated by a surgeon during an operation on a patient. The drill, in such a situation, will have to enter the patient at a precisely predetermined point and the drill must have a precisely predetermined orientation relative to the patient. It is envisaged that, from appropriate input data (for example, data from the X-ray technique described above) a computer will determine the position and the direction made by the drill. The apparatus illustrated in FIG. 2 form the operative part of a robot which is controlled by the computer 26 and which may be utilised to position the guide so that the drill may be correctly located.

Whilst it has been proposed previously to utilise robots to position operators such as drill, spray-guns and the like, such prior proposed robots have used multi-articulated arms. Whilst an arm of this type does enable a drill, spray-gun or the like to be located at any position in space, with that drill or spray-gun directed in a predetermined direction, the multi-articulation provides a not inconsiderable degree of error. In many applications the error is not a problem, but it will be appreciated that in a situation where a drilling operation is to be performed on a patient, any error is unacceptable. Thus the apparatus of FIG. 2 may be used to position a guide with a very low degree of error.

Referring now to FIG. 2 the alignment apparatus there illustrated comprises a support or base 10. The support or base may have a precisely predetermined located relative to an operating table, so that when details of the position of a patient present on the operating table have been analysed, and a specific location and orientation have been determined for a drill, a guide forming part of the apparatus may be positioned to guide the drill to that specific position with that specific orientation.

The base 10 supports two guide frames which are spaced apart and located in parallel planes. The first guide frame comprises a first vertical member 11 and a second vertical member 12 at spaced apart positions located at the rear of the base 10 as illustrated in FIG. 2. A first carriage 13 is provided which is slidable up and down the vertical member 11, and a second carriage 14 is provided which is slidable up and down the vertical member 12. A horizontal cross-beam 15 extends between the two carriages 13 and 14. The design of the vertical members 11, 12 and the carriages 13, 14 are such that the carriages may only move in synchronism, so that the horizontal cross-beam 15 is always horizontal.

A carriage 16 is provided for horizontal movement along the horizontal cross-beam 15.

The second guide frame is of a similar design, and is in a plane parallel to but spaced from the plane of the first frame. The second frame comprises two vertical members 17, 18 located at the front of the base 10 as illustrated in FIG. 2. A carriage 19 is provided for vertical movement on the vertical member 17 and a carriage 20 is provided for vertical movement on the vertical member 18. A horizontal cross-piece 21 extends between the two carriages 19 and 20, and a further carriage 22 is provided for horizontal movement on the horizontal cross-piece 1.

Again the design of the vertical member 17, 18 and the carriages 19, 20 are such that the carriages may only move in synchronism, so that the horizontal cross-piece 21 is always maintained in a horizontal position.

A tubular guide element 23 is supported on the carriages 16 and 22 which are movable along the horizontal cross members 15 and 21.

It is to be appreciated that by locating the carriages 13, 14, 19, 20, 16 and 22 at appropriate positions, the guide element 23 may be located to have any predetermined orientation and may be located at any predetermined position within the confines of the frames.

It is to be appreciated that in the described embodiment the various carriages will be moved to the desired positions by appropriate drive mechanisms 25 controlled by the computer 26, but in alternative embodiments of the invention the various horizontal members may be provided with graduations, and the horizontal cross-bars may be provided with graduations, and the various carriages may be moved to the desired positions by hand.

Whilst, in the described embodiment, the carriages on the horizontal cross-beams simply carry a tubular guide, it is to be appreciated that the carriages may, in alternate embodiments of the invention, carry an end effector, such as a drill, a spray-gun or the like.

I claim:

1. An apparatus for aligning an end effector or guide for an end effector with a predetermined point in space at a predetermined orientation, said apparatus comprising a first guide frame and a second guide frame, the first guide frame comprising two substantially vertically extending guide members, a respective carriage present for sliding movement along each of the guide members and a substantially horizontal cross-member inter-connecting the carriages, there being a further carriage mounted for horizontal movement on said horizontal cross-member and a second guide frame of similar design spaced from the first guide frame but being in a plane parallel thereto, the second guide frame comprising two substantially vertical members each provided with a respective carriage for vertical sliding movement on the respective vertical member, the two carriages being inter-connected by a second horizontal cross-member having thereon a second carriage for horizontal sliding movement on said second horizontal cross-member, the two carriages mounted for horizontal movement supporting guide means or an end effector.

2. An apparatus according to claim 1 wherein drive means are provided to drive the carriages to selected positions.

3. An apparatus according to claim 2 wherein the drive means for the carriages are computer controlled.

4. An apparatus according to claim 3 wherein the computer is provided with data from an alignment apparatus.

\* \* \* \* \*

UNITED STATES PATENT AND TRADEMARK OFFICE
CERTIFICATE OF CORRECTION

PATENT NO. : 5,603,243
DATED : February 18, 1997
INVENTOR(S) : Patrick A. Finlay It is certified that error appears in the above-indentified patent and that said Letters Patent is hereby corrected as shown below:

On the title page: Item [75]

Under [75] Inventor:

Please change "Finley" to --Finlay--.

Signed and Sealed this

Nineteenth Day of August, 1997

Attest:

BRUCE LEHMAN

*Attesting Officer*   *Commissioner of Patents and Trademarks*